United States Patent [19]

Petrohilos

[11] Patent Number: 5,009,233
[45] Date of Patent: Apr. 23, 1991

[54] MINIATURIZED HAND-HELD LASER SCANNING MICROMETER

[75] Inventor: Harry G. Petrohilos, Yellow Springs, Ohio

[73] Assignee: LaserMike, Inc., Dayton, Ohio

[21] Appl. No.: 295,272

[22] Filed: Jan. 10, 1989

[51] Int. Cl.$^5$ .............................................. A61B 5/00
[52] U.S. Cl. .................................. 128/666; 128/774; 356/387; 350/6.91
[58] Field of Search .................. 128/774, 666; 604/65, 604/67; 33/262, DIG. 21; 356/387, 386; 350/6.91

[56] References Cited

U.S. PATENT DOCUMENTS

| | | | |
|---|---|---|---|
| 2,670,651 | 3/1954 | Burns et al. | 356/386 |
| 3,765,774 | 10/1973 | Petrohilos | 356/387 |
| 3,905,705 | 9/1975 | Petrohilos | 356/387 |
| 4,007,992 | 2/1977 | Petrohilos et al. | 356/387 |
| 4,021,119 | 5/1977 | Stauffer | 356/386 |
| 4,129,384 | 12/1978 | Walker et al. | 356/381 |
| 4,131,365 | 12/1978 | Pryor | 356/387 |
| 4,217,053 | 8/1980 | Lavanchy et al. | 356/387 |
| 4,492,473 | 1/1985 | Richter et al. | 356/386 |
| 4,561,778 | 12/1985 | Kleinhuber | 356/387 |
| 4,638,169 | 1/1987 | Thomann | 356/387 |
| 4,678,337 | 7/1987 | Cohen et al. | 356/387 |

Primary Examiner—Kyle L. Howell
Assistant Examiner—Kevin Pontius
Attorney, Agent, or Firm—Killworth, Gottman, Hagan & Schaeff

[57] ABSTRACT

A miniaturized laser scanning micrometer for making precision hand-held measurements comprises a compact housing for enclosing the micrometer and defining a main body handle portion which is gripped to hold the micrometer and a scanning gap extension projecting from the main body to define a scanning gap at a distance spaced from the main body. A laser diode and collimating lens housed within the main body generate a collimated laser beam and a photocell housed within the main body detect the collimated laser beam after it has been scanned through the scanning gap. A motor driven scanner mirror receives the collimated laser beam and repeatedly scans it upon a folding mirror which directs the laser beam toward the distal end of the scanning gap extension along one side thereof. A scanner prism is positioned at the distal end of the one side of the extension, a receiver prism is positioned at the distal end of the opposite side of the extension, a scanner lens is positioned between the folding mirror and the scanner prism, and a receiver lens is positioned between the receiver prism and the photocell. Accordingly, the collimated laser beam is scanned onto the folding mirror, directed to the scanner prism through the scanner lens, scanned across the scanning gap to the receiver prism which directs the beam through the receiver lens to the photocell.

8 Claims, 2 Drawing Sheets

MINIATURIZED HAND-HELD LASER SCANNING MICROMETER

BACKGROUND OF THE INVENTION

The present invention relates generally to laser scanning micrometers which optically measure a dimension of an object and more particularly, to a miniaturized laser scanning micrometer for hand-held measurements. While the present invention is generally applicable for making precision hand-held measurements, it is particularly applicable to hand-held measurements made in an operating room to measure in vivo characteristics and specifically patency of grafted blood vessels.

Microvascular reconstructive surgery is currently limited by the ability of the plastic surgeon to assess vascular patency in vascular grafts and transplanted skin flaps. Although instrumentation is available for assessing flow in large vessels, it is not readily applicable for determining patency in microvascular systems. For example, ultrasound probes have insufficient resolution for small vessels while other devices, such as cuff flow probes, have proven to be cumbersome and unreliable. Thus, doctors must rely on their sense of "feel" for evaluation of such surgical procedures.

To overcome these difficulties and provide a usable and reliable instrument for surgeons, investigations have been performed in recent years into the use of industrial helium-neon (HeNe) laser scanning micrometers to measure, in vitro: the diameter and dynamic radial wall motion of pulsating arteries; compliance of host vessels and graft vascular prostheses; suture-line stresses; and, geometric profiles of stenotic vessels. Such investigations have been very promising and have demonstrated the ease of operation of such micrometers, their repeatability, reliability and simplicity of calibration. Unfortunately, the size, weight and scanning structure of the industrial HeNe laser scanning micrometers precludes their use as operating room instruments.

Accordingly, there is a need for a miniaturized laser scanning micrometer for performing precision hand-held measurements, for example in an operating room to measure in vivo characteristics and specifically patency of grafted blood vessels.

SUMMARY OF THE INVENTION

This need is met by a miniaturized hand-held laser scanning micrometer in accordance with the present invention wherein a scanning gap of the micrometer is extended in a narrow projection from the main body of the micrometer to facilitate taking measurements within limited spaces, such as those presented by in vivo measurements during a surgical procedure. The miniature hand-held laser scanning micrometer repeatedly scans a collimated laser beam out to and across the scanning gap of the micrometer from which it is returned to a laser beam detecting photocell for performing the measurement.

In accordance with one aspect of the present invention, a miniaturized laser scanning micrometer for making precision hand-held measurements comprises compact housing means for enclosing the miniaturized laser scanning micrometer. The housing means comprises handle means for gripping the miniaturized laser scanning micrometer and scanning gap extension means projecting from the handle means for defining a scanning gap of the miniaturized laser scanning micrometer at a distance spaced from the handle means. Laser beam generating means are housed within the handle means for generating a collimated laser beam and photocell means are housed within the handle means for detecting the collimated laser beam. Laser beam scanning means are housed within the handle means for receiving the collimated laser beam from the laser beam generating means and for repeatedly scanning the collimated laser beam through a defined optical space. Optical means housed within the handle means and the scanning gap extension means receive the collimated laser beam from the laser beam scanning means and direct the collimated laser beam across the scanning gap through the scanning gap extension means to the photocell means.

The laser beam generating means may comprise a laser diode and a laser beam collimating lens. The scanning gap extension means is substantially thinner than the handle means and tapers in width towards its distal end to facilitate taking measurements within limited spaces. The laser beam scanning means may comprise a scanner mirror and a scanner motor for rotating the scanner mirror. The scanning gap extension means may comprise a notched extension with the notch defining the scanning gap. The optical means may comprise a folding mirror for directing the laser beam toward the distal end of the notched extension along one side thereof a scanner prism positioned at the distal end of the one side of the notched extension, and a receiver prism positioned at the distal end of the side of the notched extension opposite to the one side such that the collimated laser beam is scanned onto the folding mirror, directed to the scanner prism, scanned across the scanning gap to the receiver prism which directs the beam to the photocell means. The optical means preferably further comprises a scanner lens positioned between the folding mirror and the scanner prism, and a receiver lens positioned between the receiver prism and the photocell means.

In accordance with another aspect of the present invention, a miniaturized laser scanning micrometer for making precision hand-held measurements comprises compact housing means for enclosing the miniaturized laser scanning micrometer. The housing means comprises handle means for gripping the miniaturized laser scanning micrometer and scanning gap extension means projecting from the handle means for defining a scanning gap of the miniaturized laser scanning micrometer at a distance spaced from the handle means. The scanning gap extension means defines a scanning channel extending down one side thereof and a receiving channel extending down the side opposite to the one side with the scanning gap being defined between distal ends of the scanning channel and the receiving channel. Laser beam generating means are housed within the handle means for generating a collimated laser beam and photocell means are housed within the handle means and aligned with the receiving channel for detecting the collimated laser beam. Laser beam scanning means are housed within the handle means for receiving the collimated laser beam from the laser beam generating means and for repeatedly scanning the collimated laser beam through a defined optical space. A scanner prism is positioned in the distal end of the scanning channel and a receiver prism is positioned in the distal end of the receiving channel. A folding mirror is positioned for receiving the collimated laser beam from the laser scanning means and directing the collimated laser beam to the scanner prism, the collimated laser beam then being scanned across the scanning gap to the receiving prism which in turn directs the collimated laser beam to the photocell means.

The laser beam generating means may comprise a laser diode and a laser beam collimating lens. The scanning gap extension means is substantially thinner than the handle means and tapers in width towards its distal end to facilitate taking measurements within limited spaces. The laser beam scanning means may comprise a scanner mirror and a scanner motor for rotating the scanner mirror. The miniaturized laser scanning micrometer preferably further comprises a scanner lens positioned between the folding mirror and the scanner prism, and a receiver lens positioned between the receiver prism and the photocell means.

It is thus an object of the present invention to provide a miniaturized laser scanning micrometer for performing precision hand-held measurements within limited spaces; to provide miniaturized laser scanning micrometer for performing precision hand-held measurements wherein a scanning gap of the micrometer is extended in a narrow projection from the main body of the micrometer to facilitate taking measurements within limited spaces; and, to provide a miniaturized laser scanning micrometer for performing precision hand-held measurements wherein a scanning gap of the micrometer is extended in a narrow projection from the main body of the micrometer and a collimated laser beam is repeatedly scanned out to and across the scanning gap of the micrometer from which it is returned to a laser beam detecting photocell for performing the measurements.

Other objects and advantages of the invention will be apparent from the following description the accompanying draWings and the appended claims.

DETAILED DESCRIPTION OF THE INVENTION

Figure 1:
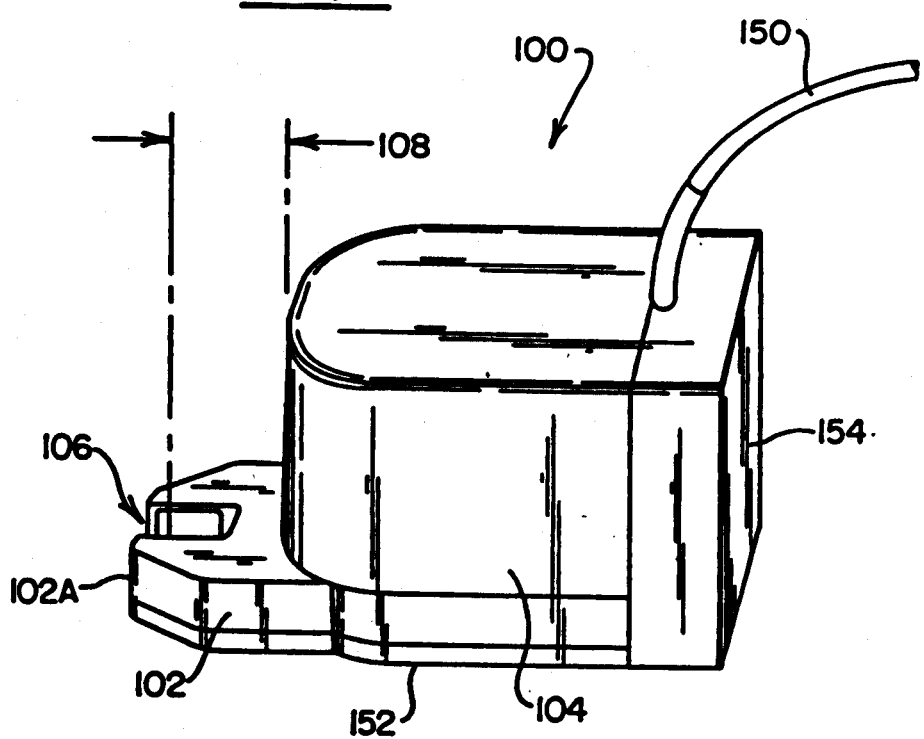
FIG. 1 is a perspective view of a miniaturized hand-held laser scanning micrometer in accordance with the present invention.

Reference is now made to the drawings wherein FIG. 1 is a perspective view of a miniaturized hand-held laser scanning micrometer 100 in accordance with the present invention for making precision hand-held measurements. A scanning gap of the micrometer 100 is extended in a narrow notched extension or projection 102 from the main body 104 of the micrometer 100 to facilitate taking measurements within limited spaces, such as those presented by in vivo measurements during a surgical procedure. The miniaturized laser scanning micrometer 100 comprises compact housing means for enclosing the micrometer 100. The housing means includes handle means generally defined by the main body 104 for gripping the micrometer 100 and scanning gap extension means generally defined by the narrow projection 102. The projection 102 defines the scanning gap 106 of the micrometer 100 at a distance 108 spaced from the main body 104.

Laser beam generating means comprising a laser diode 110 and a laser beam collimating lens 112 or lens system are housed within the main body 104 for generating a collimated laser beam 114. The collimating lens 112 is secured to an adjustable mount 115 so that the desired degree of collimation can be selected by linearly positioning the collimating lens 112 relative to the laser diode 110 along the centerline of the laser beam 114. Photocell means comprising a photocell 116 also is housed within the main body 104 for detecting the collimated laser beam 114 after it has passed across the scanning gap 106. Laser beam scanning means comprising a brushless dc motor 118, a flywheel 120 and a scanner mirror 122 mounted to the flywheel 120 for rotation therewith are housed within the main body 104 for receiving the collimated laser beam 114 from the laser diode 110 and the collimating lens 112 and repeatedly scanning the collimated laser beam 114 through a defined optical space.

Optical means are housed within the main body 104 and the projection 102 to receive the collimated laser beam 114 from the laser beam scanning means and to direct the collimated laser beam 114 across the scanning gap 106 through the projection 102 to the photocell 116. The optical means comprises a folding mirror 124 positioned within the defined optical space through which the collimated laser beam 114 is scanned for directing the laser beam 114 toward the distal end 102A of the projection 102 along one side thereof, which may be referred to as a scanning channel 102B. A scanner prism 126 is positioned at the distal end of the scanning channel 102B and a receiver prism 128 is positioned at the distal end of the side of the projection 102 opposite to the one side, which may be referred to as a receiving channel 102C.

The optical means further comprises a scanner lens 130 positioned between the folding mirror 124 and the scanner prism 126, and a receiver lens 132 positioned between the receiver prism 128 and the photocell 116. The folding mirror 124 is mounted on a rotationally adjustable mirror mount 125 so that the angle between the outermost scans 114A and 114B is bisected by an optical axis 130A of the scanner lens 130 which is secured to a mount 131 linearly adjustable along the axis 130A.

By adjusting the mount 131 along the optical axis 130A, the focal point of the scanner lens 130 can be made coincident with the intersection of the laser beam 114 and a reflecting surface of the scanner mirror 122. This adjustment results in the laser beam 114 exiting the scanner lens 130 parallel to the optical axis 130A at all times. The collimated laser beam 114 is scanned onto the folding mirror 124, directed to the scanner prism 126 through the scanner lens 130, scanned across the scanning gap 106 to the receiver prism 128 which directs the beam 114 through the receiver lens 132 to the photocell 116. The optical means and laser beam means are mounted on an optical platform 138 which extends through and interconnects the main body 104 and the extension 102 to stabilize the optical portion of the micrometer 100 in accordance with standard techniques. The laser beam scanning means must then be mounted adjacent to and properly aligned with the optical platform 138 to ensure proper operation of the micrometer 100.

A laser diode power supply 140 is designed to supply current to the laser diode 110 so that emitted optical power is substantially constant. Part of the emissions from the laser diode 110 is sampled by means of a photodiode which is an internal part of the laser diode 110 and compared to a reference voltage. Supply current to the laser diode 110 is then controlled to maintain the difference between the sampled emissions and the reference voltage at a low level despite variations in supply voltage, operating temperatures, aging of the laser diode 110 and other variables which can effect emissions.

An object 142 to be measured, such as a grafted blood vessel, is placed within the scanning gap 106 defined between the scanner prism 126 and the receiver prism 128 in the notch or open area of the projection 102. As the laser beam 114 is scanned in parallel across the scanning gap 106, it is interrupted by the object 142. The scan beams are redirected by the receiver prism 128 through the receiver lens 132 to focus them onto the photocell 116 which is secured to a mount 144 adjustable along an optical axis 132A of the receiver lens 132. The mount 144 may be adjusted so that the focal point of the receiver lens 132 is coincident with an active area of the photocell 116 such that only rays which are parallel to the optical axis 132A of the receiver lens 132 are sensed by the photocell 116.

Figure 2:
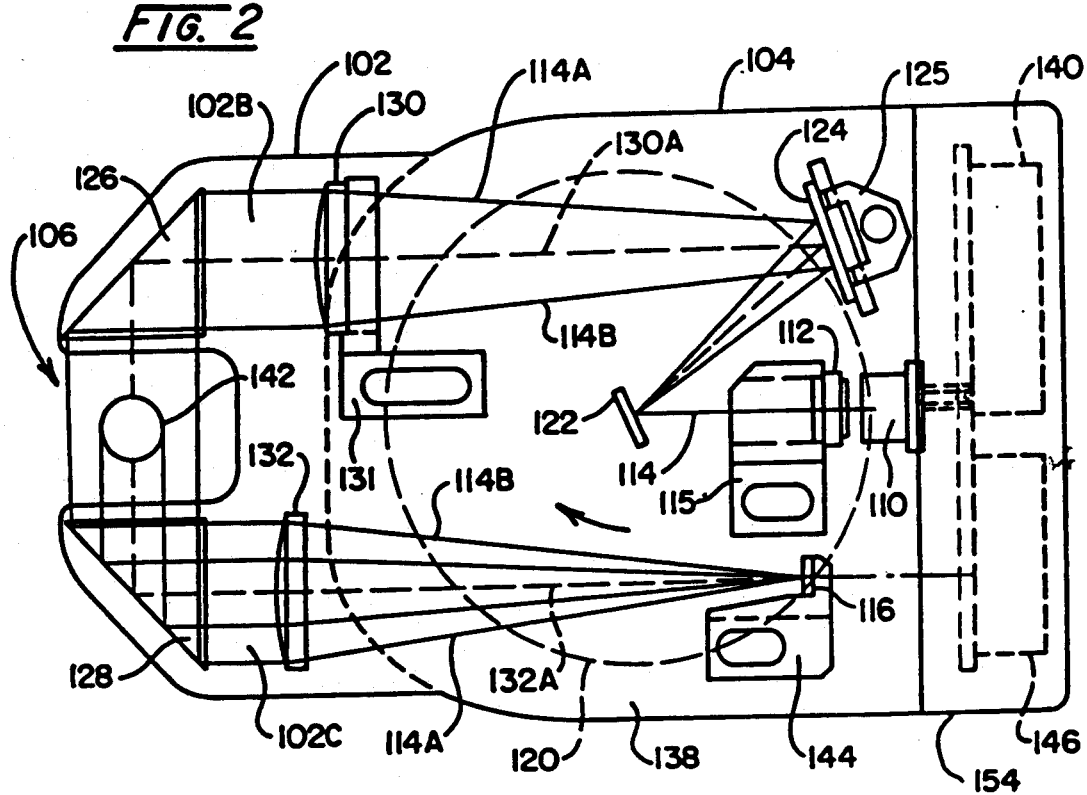
FIG. 2 is a bottom view of the laser scanning micrometer as shown in FIG. 1 with an optical cover removed to expose the optics of the micrometer.
Figure 3:
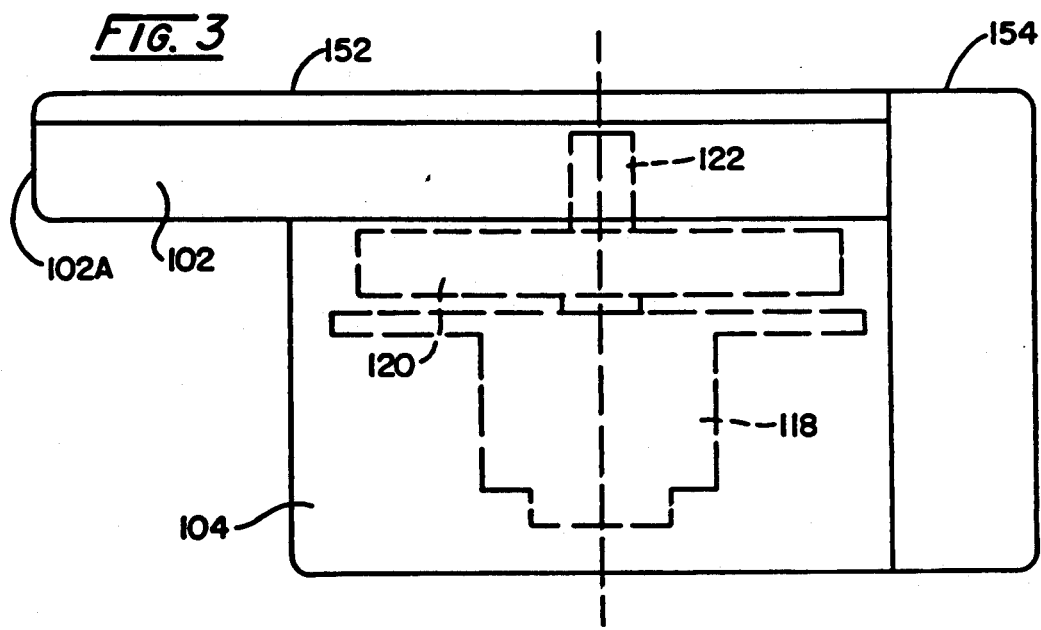
FIG. 3 is a side view of the hand-held laser scanning micrometer of FIG. 2.

Output signals from the photocell 116 are initially processed by circuitry 146 and then passed via a cable 150 (see FIG. 1) to external instrumentation (not shown) which determines the dimensions of the object 142 in accordance with known techniques as described for example in U.S. Pat. Nos. 3,765,774, No. 3,905,705, and No. 4,007,992 which may be referred to for additional details and are incorporated herein by reference. The cable 150 also carries power to the micrometer 100. An optical cover 152, removed in FIG. 2, and an electronics cover 154 isolate and protect all optical and electronic parts from the external environment.

Having thus described the miniaturized hand-held laser scanning micrometer of the present invention in detail and by reference to preferred embodiments thereof, it will be apparent that modifications and variations are possible without departing from the scope of the invention defined in the appended claims.

What is claimed is:

1. A miniaturized laser scanning micrometer for making precision hand-held measurements comprising:
   compact housing means for enclosing said miniaturized laser scanning micrometer, said housing means comprising handle means for gripping said miniaturized laser scanning micrometer and scanning gap extension means projecting from said handle means for defining a scanning gap of said miniaturized laser scanning micrometer at a distance spaced from said handle means, said scanning gap extension means being substantially thinner than said handle means and tapering in width towards its distal end to facilitate insertion of said scanning gap extension means into limited spaces to permit taking measurements therewithin;
   laser beam generating means housed within said handle means for generating a collimated laser beam;
   photocell means housed within said handle means for detecting said collimated laser beam;
   laser beam scanning means housed within said handle means for receiving said collimated laser beam from said laser beam generating means and repeatedly scanning said collimated laser beam through a defined optical space; and
   optical means housed within said handle means and said scanning gap extension means for receiving said collimated laser beam from said laser beam scanning means and directing said collimated laser beam across said scanning gap through said scanning gap extension means to said photocell means.

2. A miniaturized laser scanning micrometer as claimed in claim 1 wherein said laser beam generating means comprises a laser diode and a laser beam collimating lens.

3. A miniaturized laser scanning micrometer as claimed in claim 1 wherein said laser beam scanning means comprises a scanner mirror and a scanner motor for rotating said scanner mirror.

4. A miniaturized laser scanning micrometer as claimed in claim 1 wherein said scanning gap extension means comprises a notched extension with said notch defining said scanning gap.

5. A miniaturized laser scanning micrometer as claimed in claim 4 wherein said optical means comprises a folding mirror for directing said laser beam toward the distal end of said notched extension along one side thereof, a scanner prism positioned at the distal end of said one side of said notched extension, a receiver prism positioned at the distal end of the side of said notched extension opposite to said one side, a scanner lens positioned between said folding mirror and said scanner prism, and a receiver lens positioned between said receiver prism and said photocell means such that said collimated laser beam is scanned onto said folding mirror, directed to said scanner prism through said scanner lens, scanned across said scanning gap to said receiver prism which directs said beam through said receiver lens to said photocell means.

6. A miniaturized laser scanning micrometer for making precision hand-held measurements comprising:
   compact housing means for enclosing said miniaturized laser scanning micrometer, said housing means comprising handle means for gripping said miniaturized laser scanning micrometer and scanning gap extension mean projecting from said handle means for defining a scanning gap of said miniaturized laser scanning micrometer at a distance spaced from said handle means, said scanning gap extension means being substantially thinner than said handle means and tapering in width towards its distal end to facilitate insertion into limited spaces for taking measurements therewithin and defining a scanning channel extending down one side thereof and a receiving channel extending down the side opposite to said one side with said scanning gap being defined between distal ends of said scanning channel and said receiving channel;
   laser beam generating means housed within said handle means for generating a collimated laser beam;
   photocell means housed within said handle means and aligned with said receiving channel for detecting said collimated laser beam;
   laser beam scanning means housed within said handle means for receiving said collimated laser beam from said laser beam generating means and repeatedly scanning said collimated laser beam through a defined optical space;
   a scanner prism positioned in the distal end of said scanning channel;
   a receiver prism positioned in the distal end of said receiving channel;
   a scanner lens positioned between said folding mirror and said scanner prism;
   a receiver lens positioned between said receiver prism and said photocell means; and a folding mirror for receiving said collimated laser beam from said laser scanning means and directing said collimated laser beam to said scanner prism through said scanner lens, said collimated laser beam then being scanned across said scanning gap to said receiver prism which in turn directs said collimated laser beam through said receiver lens to said photocell means.

7. A miniaturized laser scanning micrometer as claimed in claim 6 wherein said laser beam generating means comprises a laser diode and a laser beam collimating lens.

8. A miniaturized laser scanning micrometer as claimed in claim 7 wherein said laser beam scanning means comprises a scanner mirror and a scanner motor for rotating said scanner mirror.

* * * * *